(12) United States Patent
Chassard et al.

(10) Patent No.: US 9,828,155 B2
(45) Date of Patent: Nov. 28, 2017

(54) CARDBOARD-BOX-FREE PACKAGING OF SOLID YEAST PRODUCTS

(71) Applicant: LESAFFRE ET COMPAGNIE, Paris (FR)

(72) Inventors: Jean-Pierre Chassard, Blaesheim (FR); Stéphane Lacroix, Talmont Saint Hilaire (FR); Bernard Stadler, Strasbourg (FR); Sophie Schneider, Eschau (FR)

(73) Assignee: LESAFFRE ET COMPAGNIE, Paris (FR)

( * ) Notice: Subject to any disclaimer, the term of this patent is extended or adjusted under 35 U.S.C. 154(b) by 0 days.

(21) Appl. No.: 15/288,314

(22) Filed: Oct. 7, 2016

(65) Prior Publication Data
US 2017/0036834 A1 Feb. 9, 2017

Related U.S. Application Data

(60) Division of application No. 13/495,354, filed on Jun. 13, 2012, now abandoned, which is a
(Continued)

(30) Foreign Application Priority Data

Dec. 14, 2009 (FR) ...................................... 09 58921

(51) Int. Cl.
*B65D 71/00* (2006.01)
*B65D 77/04* (2006.01)
(Continued)

(52) U.S. Cl.
CPC .......... *B65D 71/0096* (2013.01); *A23L 31/10* (2016.08); *B65B 5/06* (2013.01);
(Continued)

(58) Field of Classification Search
CPC .. B65D 71/0069; B65D 77/042; B65D 81/18; B65D 81/24; B65D 81/267; A23L 31/10;
(Continued)

(56) References Cited

U.S. PATENT DOCUMENTS 2,081,724 A   5/1937 Abbott
2,430,459 A  11/1947 Farrell et al.
(Continued)

FOREIGN PATENT DOCUMENTS

EP   2 055 639   5/2009
GB   1233902     6/1971

OTHER PUBLICATIONS

Poly Print, Yield and Unit Weight, [on line] 2008, retrieved May 8, 2016 URL:<http://www.polyprint.com/flexographic-yield.htm>.

*Primary Examiner* — Erik Kashnikow
*Assistant Examiner* — Chaim A Smith
(74) *Attorney, Agent, or Firm* — Vedder Prices P.C.; Thomas J. Kowalski; Deborah L. Lu

(57) ABSTRACT

The invention relates to packaging (10) for solid yeast products, such as: a supporting element (12); solid yeast products contained in one or more packages (22), supported by the supporting element (12); and an outer cover (14) retaining all of the solid yeast products contained in the packages (22) on the supporting element (12). According to the invention, all of the packages (22) located between the solid yeast products and the outer cover (14) may have a surface density no greater than 200 g/m². The invention also relates to a method for packaging solid yeast products and to a method for preserving and using solid yeast products thus packaged.

13 Claims, 5 Drawing Sheets

Related U.S. Application Data continuation-in-part of application No. PCT/IB2010/055727, filed on Dec. 10, 2010.

(51) Int. Cl.
| | |
|---|---|
| *B65D 81/18* | (2006.01) |
| *B65D 81/24* | (2006.01) |
| *B65D 81/26* | (2006.01) |
| *A23L 31/10* | (2016.01) |
| *B65B 5/06* | (2006.01) |
| *B65B 13/02* | (2006.01) |
| *B65B 63/02* | (2006.01) |
| *C12N 1/04* | (2006.01) |
| *C12N 1/16* | (2006.01) |

(52) U.S. Cl.
CPC ............... *B65B 13/02* (2013.01); *B65B 63/02* (2013.01); *B65D 77/042* (2013.01); *B65D 81/18* (2013.01); *B65D 81/24* (2013.01); *B65D 81/267* (2013.01); *C12N 1/04* (2013.01); *C12N 1/16* (2013.01); *A23V 2002/00* (2013.01)

(58) Field of Classification Search
CPC ........... B65B 5/06; B65B 13/02; B65B 63/02; C12N 1/04; C12N 1/16
See application file for complete search history.

(56) References Cited

U.S. PATENT DOCUMENTS

| | | |
|---|---|---|
| 2,441,477 A | 5/1948 | Farrell |
| 3,348,673 A | 10/1967 | Bahls et al. |
| 3,522,688 A | 8/1970 | Kaliwoda et al. |
| 3,529,717 A | 9/1970 | McDougal |
| 3,825,113 A | 7/1974 | Kramer et al. |
| 3,858,526 A | 1/1975 | Lombard et al. |
| 3,945,493 A | 3/1976 | Cardinal |
| 3,986,611 A | 10/1976 | Dreher |
| 4,136,501 A | 1/1979 | Connolly |
| 4,206,846 A | 6/1980 | Connolly |
| 5,116,191 A | 5/1992 | Van |
| 2007/0092602 A1* | 4/2007 | Degre ............... A21D 2/16 426/20 |
| 2012/0061391 A1 | 3/2012 | Sambrailo et al. |

* cited by examiner

CARDBOARD-BOX-FREE PACKAGING OF SOLID YEAST PRODUCTS

RELATED APPLICATIONS AND INCORPORATION BY REFERENCE

This application is a divisional of U.S. application Ser. No. 13/495,354 filed Jun. 13, 2012, which is a Continuation-in-part application of International Patent Application Serial Number PCTAB2010/055727 filed Dec. 10, 2010, which published as PCT Publication No. WO 2011/073869 on Jun. 23, 2011, which claims benefit of French patent application Serial No. 09/58921 filed Dec. 14, 2009.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a package of solid yeast products. It further relates to a method of packaging yeast products. It further relates to a method of storing and using solid yeast products.

BACKGROUND OF THE INVENTION

Yeast products, notably those available in solid form (particularly compressed yeast), are particularly sensitive to their storage conditions, notably the temperature, and are particularly exposed to contamination. They are thus products which are difficult to package, and which require storage conditions which allows the maintenance of both their microbiological qualities and their performance (notably in terms of fermentation power) in order to secure the organoleptic quality of the bread-making products prepared from them.

In fact, the storage of solid yeast products in inappropriate conditions, or changes in the storage conditions, may have effects on yeast metabolism level. Therefore, an increase of the fermentation metabolism and/or respiratory metabolism causes a considerable production of gas and spontaneous heating of the products. This may lead to a degradation of the microbiological quality and the performance (notably in terms of fermentation power) of the yeast products, and therefore a degradation of the organoleptic qualities of the bread-making products obtained from them.

In particular, a rise in the surrounding temperature can result in an increase in the metabolism of yeasts, itself leading to a supplementary evolution of heat. In this way, an undesirable "chain reaction" can be established; it is therefore useful to provide packaging for solid yeast products which allows efficient cooling.

For example, there are known solid yeast products, also called "breads" ("pains"), either packaged individually in paper or left unpackaged, which are then grouped together and wrapped to form what are known as packs, protected with cellophane. Typically, the packs have a weight of approximately 2.5 kg. Typically, the packs are then grouped in sets of four in cardboard boxes having a weight of approximately 10 kg each. The boxes are finally palletized in crossed layers to form a package.

Since cardboard is a good thermal insulator, the method of packaging solid yeast products used at present has the drawback of not allowing completely satisfactory cooling of the solid yeast products.

In order to reduce this drawback, short bands are generally provided on the tops of the boxes in order to create an opening to facilitate contact with the external air; and, there is no overall packaging of the boxes on the pallet. However, this leads to risks of contamination of the products. Furthermore, the degree of cooling of the solid yeast products is not entirely satisfactory.

There is thus a real need to provide packaging which can preserve and maintain the qualities of solid yeast products, by allowing notably satisfactory cooling of the solid yeast products while reducing the risks of their contamination.

Citation or identification of any document in this application is not an admission that such document is available as prior art to the present invention.

SUMMARY OF THE INVENTION

The invention firstly relates to a package of solid yeast products which may comprise:
- a support element;
- solid yeast products contained in one or more packagings, supported by the support element;
- an outer covering maintaining the whole solid yeast products contained in the packagings on the support element;

wherein the totality of the packagings present between the solid yeast products and the outer covering may have a mass per unit surface area less than or equal to 200 $g/m^2$.

According to one embodiment, the totality of the packagings present between the solid yeast products and the outer covering may have:
- a mass per unit surface area less than or equal to 150 $g/m^2$, preferably less than or equal to 100 $g/m^2$, and more particularly preferably less than or equal to 80 $g/m^2$; and/or
- a thickness less than or equal to 150 μm, preferably less than or equal to 120 μm, and more particularly preferably less than or equal to 90 μm.

According to one embodiment, the packagings may be made of materials chosen from cellophane, paper, food-grade plastic film, and textile, and preferably chosen from cellophane and paper.

According to one embodiment, the outer covering may be made of a stretchable plastic material, preferably single-stretched or double-stretched polyethylene.

According to one embodiment, the solid yeast products may be grouped in packs, each pack being contained in at least one packaging, and the packs may be preferably grouped into batches, the packs of each batch may be preferably tied between them, preferably by means of one or more connecting bands.

According to one embodiment:
- spaces may be provided between at least one part of the batches; or
- the whole batches may be arranged without spaces between them.

According to one embodiment, the batches may be positioned on the support element in a plurality of superimposed layers.

According to one embodiment, the package may comprise five layers, and:
- each layer may comprise ten batches;
- each batch may comprise six packs, preferably distributed in three rows of two packs each, the packs of each batch being preferably tied by two connecting bands essentially parallel and two connecting bands other essentially parallel which cross over the preceding ones; and
- each pack may comprise five solid yeast products.

According to one embodiment, the solid yeast products may be compressed yeast, preferably which may comprise 27% to 34% of dry matter.

The invention also relates to a method of packaging solid yeast products, which may comprise the following steps:
- the provision of a support element;
- the packaging of solid yeast products in one or more packagings;
- the placing on the support element of the solid yeast products contained in the packagings;
- the placing of an outer covering around the whole solid yeast products contained in the packagings;

and wherein the totality of the packagings present between the solid yeast products and the outer covering may have a mass per unit surface area less than or equal to 200 g/m$^2$.

According to one embodiment, the totality of the packagings present between the solid yeast products and the outer covering may have:
- a mass per unit surface area less than or equal to 150 g/m$^2$, preferably less than or equal to 100 g/m$^2$, and more particularly preferably less than or equal to 80 g/m$^2$; and/or
- a thickness less than or equal to 150 µm, preferably less than or equal to 120 µm, and more particularly preferably less than or equal to 90 µm.

According to one embodiment:
- the packagings are made of materials chosen from cellophane, paper, food-grade plastic film, and textile, and preferably chosen from cellophane and paper; and/or
- the outer covering is made of a stretchable plastic material, preferably single-stretched or double-stretched polyethylene.

According to one embodiment, the method may comprise, before the step of placing on the support element the solid yeast products contained in the packagings:
- a step of grouping the solid yeast products into packs, each pack being contained in at least one packaging; and
- a step of grouping the packs into batches, the packs of each batch being preferably tied between them, preferably by means of one or more connecting bands;

and, preferably, the step of placing on the support element the solid yeast products contained in the packagings may comprise the placing of the batches on the support element in superimposed layers.

In one embodiment, when placing on the support element the solid yeast products contained in the packagings:
- spaces are provided between the batches; or
- the whole batches are arranged without spaces between them.

In one embodiment, the solid yeast products are compressed yeast, preferably which may comprise 27% to 34% of dry matter.

The invention also relates to a method for storing and using solid yeast products, which may comprise the following steps:
- packaging solid yeast products in a package as described above, preferably according to a packaging method described above;
- storing said package of solid yeast products, until their use, at an external temperature less than or equal to 15° C., preferably less than or equal to 10° C., and more particularly preferably less than or equal to 5° C.;
- using at least one of the solid yeast products.

According to one embodiment, the solid yeast products are transported during the storage step, and the storage step preferably has a duration comprised between one day and 7 weeks, and preferably between one week and 7 weeks.

According to one embodiment, the temperature of each solid yeast product remains less than or equal to 15° C., preferably less than or equal to 12° C., and more particularly preferably less than or equal to 10° C. during the storage step.

According to one embodiment, at least one solid yeast product is used for the production of a bread-making product.

The present invention allows overcoming the drawbacks of the prior. It provides, more particularly, a package of solid yeast products which allows the cooling of the solid yeast products during their storage, while, at the same time, reducing the risks of contamination of the products. The maintenance of the microbiological quality and the performance of these products (notably their fermentation power) is thus achieved, together with the maintenance of the organoleptic qualities of the bread-making products made from the yeast products.

This is achieved by means of the cardboard-box-free packaging of the solid yeast products, in other words by using only relatively thin packagings, wherein the whole wrapped solid yeast products is maintained on a support element by means of an outer covering.

Thus the package according to the invention provides a lower level of thermal insulation than that of the prior art, in relation to the solid yeast products. It therefore allows a better cooling of the solid yeast products, while avoiding problems of contamination.

According to certain specific embodiments, the invention also has one, or preferably more than one, of the advantageous characteristics listed below.

- In prior art packages, it is essential to provide spaces between the cardboard boxes to form cooling passages assuring heat exchange between the solid yeast products contained in the cardboard boxes and the air flowing through the passages. The invention allows being dispensed of the cooling passages if desired, this allowing increasing the stability of the package to be increased, particularly during transport.
- In prior art packages, it is essential to provide a bonding of the batches of products between them and on the pallet (using palletizing adhesive), in order to maintain the wholebatches in place on the pallet. However, the presence of adhesive increases the risk of contamination of the products. The invention allows being dispensed of any bonding of the product batches between them and on the pallet, and therefore limits the risk of contamination.
- A packaging using cardboard box requires the customer to remove and fold the cardboard boxes. The cardboard boxes must then be stored, sent to a collecting point and compacted, and the collections must be supervised.

These operations generate labor costs and waste management costs which are greatly reduced by the use of packaging according to the invention.

Packaging enclosures made of materials with a high mass per unit surface area, such as cardboard, do not help to reduce packaging according to the current law. The packaging of the invention therefore allows a better protection of the environment than the prior art packaging.

In food production facilities, cardboard is criticized as a critical potential factor in cross-contamination. It often fails to be in conformity with the health regulations imposed to the users of the solid yeast products, notably baking enterprises. The package of the invention warranties a better hygiene, due to the absence of utilization of cardboard box.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

The invention relates to packaging of solid yeast products. Throughout the following text, the term "solid yeast product" refers to any product containing yeasts, which tends to conserve essentially its shape even when it is not in any kind of container. Thus solid yeast products are distinguished from liquid yeast products (yeast suspensions, yeast cream . . . ) and powdered yeast products (dried yeast). Preferably, solid yeast products contain live yeasts.

Solid yeast products are generally in the form of compact blocks. Solid yeast products may be breads of compressed yeast. Solid yeast products contain preferably 27% to 34% of dry matter.

Figure 1:
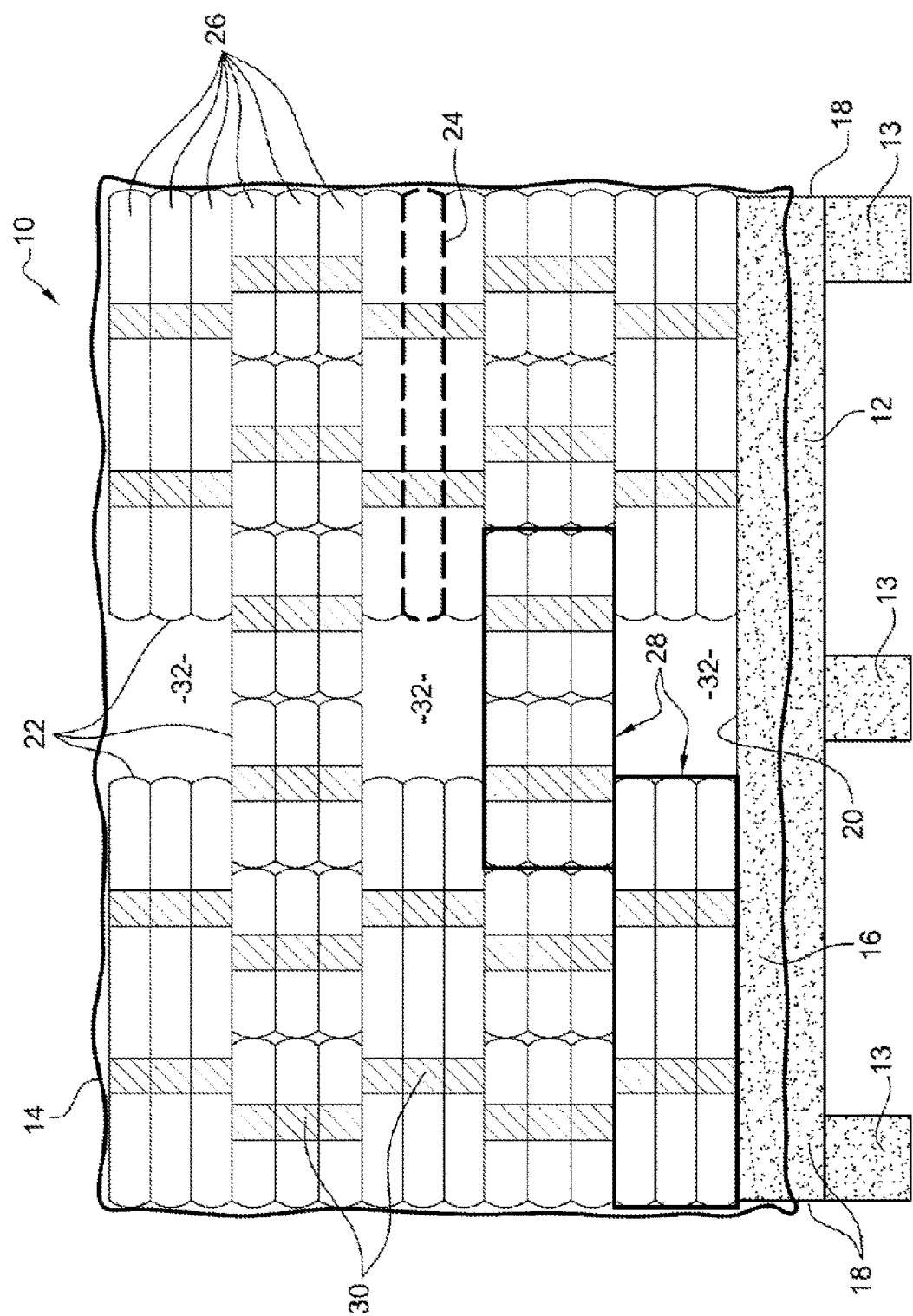
FIG. 1 is a diagram of an example of a package according to the invention.

Reference will now be made to FIG. 1, which presents a diagram of an example of a package 10 according to the invention, viewed from the front.

The package 10 of solid yeast products may comprise a support element 12. The support element 12 allows the supporting of the solid yeast products. It may have supporting feet 13. It also generally may comprise a support plate or, in a preferred embodiment, a set of transverse and longitudinal bars or planks tied to each other. This second solution assures an air passage through the lower face of the package (between the bars of the support element 12) and therefore permits better cooling of the solid yeast products.

The support element can be of general parallelepipedal shape, which allows optimal arrangement of the package when it is stored with other packages. It can be a handling pallet, which allows the transport of the package by a trolley adapted for transport of pallets (a pallettrolley). The support element 12 can be made of wood. A wooden support element has the advantage of low production cost. Wood can also allow some humidity absorption of humidity. The support element 12 can be made of plastic material, which may be advantageous in case of significant condensation, since plastic is not affected by the presence of water.

The package 10 may comprise an outer covering 14 maintaining the wholesolid yeast products on the support element 12. This outer covering 14 can be a plastic film applied around the whole solid yeast products so as to exert on the products a pressure which maintains them on the support element 12, and possibly maintaining them tightened between them.

The stacking of the solid yeast products on the support element 12 defining an upper surface and a lateral surface (the latter being, for example, composed of four faces, if the stacking is of essentially parallelepipedal shape), the outer covering 14 covers whole the lateral surface of the stack, and if necessary also covers some or all of the upper surface thereof.

The outer covering 14 can also be applied to a part 16 of the support element 12. If the support element 12 is of generally parallelepipedal shape, the packaging can be applied to an upper part 16 of the four lateral faces 18 of the support element 12, the solid yeast products being supported by the upper face 20 of the support element 12. Alternatively, connecting bands can be provided to surround the outer covering 14 and the support element 12, in order to tie them together.

The outer covering 14 can, notably, be made of any plastic film intended for the packaging of food products. The outer covering 14 can be made of a stretchable material, preferably a stretchable plastic material. It can, notably, be made of polyethylene and can, in particular, be made of single-stretched or double-stretched polyethylene. The outer covering 14 can be heat-shrinkable. The outer covering 14 can also be any film used in the methods of palletizing known in the prior art. According to a particular embodiment, the outer covering 14 is composed of a plastic film relatively permeable to gases and particularly to water vapor, in order to avoid the condensation of water on the surface of the covering and in order to allow the better cooling of the products.

The package 10 may comprise one or more packagings 22 between the solid yeast products and the outer covering 14. A packaging 22 refers to any structure which surrounds or envelops a yeast product or a plurality of yeast products (which themselves may or may not be wrapped), that is to say, a structure which isolates or separates them from the outside.

An example 24 of a packaging surface 22 is shown in bold broken lines in FIG. 1. The individual solid yeast products which are located inside the packagings 22 are not visible in FIG. 1.

The packagings can be made of any solid material in the form of sheet or film which is capable of protecting the solid yeast products from any contact with the environment. This material can be partially gas-permeable, and even liquid-permeable, in order to avoid problems of swelling (due to the emission of gases) or of water condensation. Alternatively, an impermeable material may be chosen and small openings (or pores) may be provided to allow exchanges with the external environment. Preferably, the packagings 22 are completely sealed (and are, in particular, impermeable to micro-organisms). The packagings 22 are preferably flexible, but can possibly be rigid.

A packaging 22 can contain one or more solid yeast products directly, and/or can contain one or more other packagings 22. Thus it is possible, for example, to group a plurality of solid yeast products together in at least one packaging, and to combine a plurality of these groups between them in at least another packaging.

Each solid yeast product is thus contained in, or surrounded by, at least one packaging 22, and possibly a plurality of packagings.

Thus the support element 12 does not support directly the solid yeast products, but supports the packagings 22 which contain them. In the same way, the outer covering 14 does not maintain directly the solid yeast products on the support element 12, but it maintains the packagings 22 which contain them.

All the packagings 22 between the solid yeast products and the outer covering 14 have a mass per unit surface area (or "paper density") less than or equal to 200 g/m². In other words, each packaging 22 located inside the outer covering 14, and each structure corresponding to a packaging 22 (according to the definitions given above), has a mass per unit surface area of less than 200 g/m².

Alternatively or additionally, all the packagings 22 between the solid yeast products and the outer covering 14 have a thickness less than or equal to 150 µm. In other words, each packaging 22 located inside the outer covering 14, and each structure resembling a packaging 22 (according to the definitions given above), has a thickness less than or equal to 150 µm.

In other words, no packaging with a mass per unit surface area of more than 200 g/m² is present inside the outer covering 14; in particular, no cardboard packaging is present inside the outer covering 14 (cardboard being defined as having a mass per unit surface area of more than 224 g/m²). Alternatively, no packaging with a thickness of more than 150 µm is present inside the outer covering 14; in particular, no cardboard packaging is present inside the outer covering 14 (since cardboard is defined as having a thickness of more than 175 µm).

Consequently, the present description can also be read by replacing systematically the criterion of mass per unit surface area less than or equal to 200 g/m², with the criterion of a thickness less than or equal to 150 µm.

Preferably, the outer covering 14 has the same characteristics of mass per unit surface area (or thickness) as the packagings 22.

Because of the low paper density (or low thickness) of the packagings 22, a good level of heat exchange is permitted between the solid yeast products and the external air, and thus good cooling of the solid yeast products. This better cooling is related to the possibility of isolating the solid yeast products more completely than in the prior art (the cardboard boxes being open in the prior art). This allows reducing the risk of contamination of the products.

Furthermore, the cooling passages between the packagings 22 are possible, but are not essential, according to the invention, by contrast with the prior art. More generally, the invention allows avoiding all the whole aforementioned drawbacks related to the presence of cardboard.

The outer covering 14 advantageously protects the solid yeast products against all contamination; the use of this outer covering 14 enclosing all the products is made possible by the absence of any packagings with a high paper density (cardboard) from the package.

Generally, as the paper density of the packagings 22 is low and/or as the thickness of the packagings 22 is low, the aforementioned advantages become more marked. Thus, the totality of the packagings 22 between the solid yeast products and the outer covering 14 can have a mass per unit surface area which is less than or equal to 150 g/m², preferably less than or equal to 120 g/m², preferably less than or equal to 100 g/m², preferably less than or equal to 80 g/m², preferably less than or equal to 70 g/m², preferably less than or equal to 60 g/m², preferably less than or equal to 55 g/m², preferably less than or equal to 50 g/m², preferably less than or equal to 45 g/m². Alternatively or additionally, the totality of the packagings 22 between the solid yeast products and the packaging 14 can have a thickness which is less than or equal to 120 µm, preferably less than or equal to 90 µm, preferably less than or equal to 70 µm, preferably less than or equal to 60 µm, preferably less than or equal to 50 µm, preferably less than or equal to 40 µm, preferably less than or equal to 35 µm.

Generally, as the paper density of the packaging is high and/or as their thickness is high, the stiffness of the packagings 22 increases. Thus, all the packagings 22 between the solid yeast products and the outer covering 14 can have a mass per unit surface area greater than or equal to 5 g/m², preferably greater than or equal to 10 g/m², preferably greater than or equal to 15 g/m², preferably greater than or equal to 20 g/m². Alternatively or additionally, all the packagings 22 between the solid yeast products and the outer covering 14 can have a thickness greater than or equal to 5 micrometers, preferably greater than or equal to 10 micrometers, preferably greater than or equal to 15 micrometers, preferably greater than or equal to 20 micrometers.

The packagings 22 can be made of cellophane and/or paper. Indeed, this is because these materials have satisfactory stiffness although they have a low mass per unit surface area and a low thickness. They are impermeable to micro-organisms and semi-permeable to gases and liquids. The cellophane can be transparent, which can allow inspecting visually the solid yeast products without removing them from the packaging. It is furthermore an advantageous material since it is not affected by humidity. Alternatively, the packagings 22 can be made of partially permeable food-grade plastic material or of textile material. Typically, the solid yeast products can be distributed in single packagings 22 made of cellophane, or in two superimposed (concentric) packagings 22, respectively made of cellophane and of paper.

In the embodiment shown in FIG. 1, the solid yeast products are grouped in packs 26, each pack 26 being inside a packaging 22 (or in two superimposed packagings 22). The packs 26 are grouped into batches 28 in order to improve the stability of the package. Each batch 28 can be contained in a packaging, or, preferably, as shown in FIG. 1, the batches 28 can be formed by tying the packs 26 by means of one or more connecting bands 30: thus this avoids the presence of supplementary packaging and facilitates the cooling of the products. In the example of FIG. 1, two of the batches 28 have been highlighted by bold lines.

A connecting band is a long and narrow tying means which can be closed onto itself so as to encircle a plurality of packs 26. Since it does not completely cover the surface of the batch 28, the connecting band 30 is not considered to be a packaging 22. The connecting bands 30 can be made, for example, of paper, of plastic material, of cardboard or of textile material. The connecting bands 30 are preferably made of moisture-resistant material. The connecting bands 30 are sufficiently narrow not to disturb the cooling of the solid yeast products. Tying the packs 26 with connecting bands 30 allows transporting the batches 28 of packs 26 thus formed, with the connecting bands 30 forming handles. The connecting bands 30 can include means for their fast removal by the user who therefore did not need to use any special tools. The connecting bands 30 can be stiff in order to avoid forming an impression on the solid yeast products.

The solid yeast products can be grouped into packs 26 in such a way that the packs 26 have an essentially parallel-epipedal shape, with a length at least one and a half times, or preferably at least twice, as great as the width and/or the height. In this case, the packs 26 are tied in batches 28 in such a way that the lengths of the packs 26 of a batch 28 lie in the same direction. This configuration confers a good degree of stability to each batch 28.

The packs 26 can include a weld, notably if the packagings 22 are made of cellophane. The packs can then be positioned head to tail in the batches 28, in such a way that the welds of two packs 26 are not in contact. This avoids that the frictions between packagings 22 do not open the welds during the transport of the package 10.

As shown in the example of FIG. 1, spaces 32 can be provided between the batches 28. These spaces 32 (cooling passages) can improve the cooling of the solid yeast products.

Conversely, the batches 28 can be tightened to one another. This configuration allows an optimal use of the surface area offered by the support element 12 and permits a greater stability during the transport of the package 10.

Figure 2:
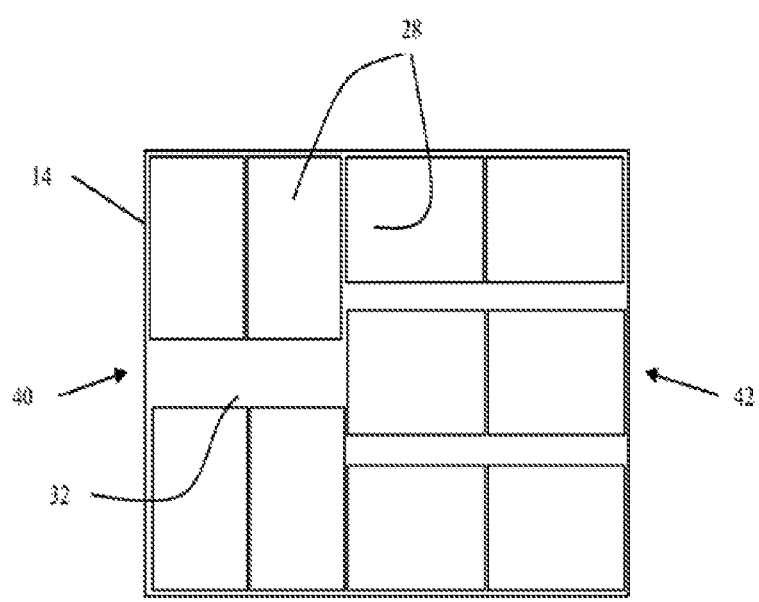
FIG. 2 is a diagram of a detail of a package according to the invention.

As shown in the example of FIG. 1, the batches 28 can be arranged on the support element 12 in a plurality of layers. This allows a better use of the space above the support element 12. An example of package with ten batches 28 per layer is shown in FIG. 2, which is a diagram of a layer viewed from above.

In this example, four batches 28 are arranged longitudinally in the direction of the width of the package, in a first part 40 of the layer. The other six batches 28 are arranged longitudinally in the direction of the length of the package, in a second part 42 of the layer. A space 32 is here provided in the first part 40, between the batches 28.

As can be observed in FIG. 1, the layers of the package can be crossed. In other words, the first part 40 of a lower layer is arranged directly below the second part 42 of the layer located directly above this lower layer, and vice versa. This results in an alternation of the layer configurations in the vertical direction. This ensures that all the batches are in contact with a space 32 of cooling (when such spaces are present). It also assures the better stability of the package.

The packs 26 can, for example, group 4 to 6 solid yeast products and can have a weight of 2 to 3 kg. The batches 28 can, for example, have a weight of 10 to 20 kg. The package 10 can, for example, have a total weight of 700 to 800 kg. The total weight can however exceed 800 kg, notably in the case in which the package may comprise more than five layers.

In the example of FIG. 1, the package 10 (of about 750 kg) may comprise five layers. Each pack 26 (of about 2.5 kg) may comprise five solid yeast products (cakes of yeast weighing approximately 500 g each). Each batch 28 (of about 15 kg) may comprise six packs 26, preferably arranged in three rows of two packs. The packs 26 of a batch 28 are preferably tied by two connecting bands 30 essentially parallel and two other connecting bands 30 essentially parallel which cross over the preceding ones. Each layer may comprise ten batches 28. This configuration of the package 10 provides a good compromise between maneuverability, optimal use of space, and stability.

A lower interleaved element can be provided between the support element 12 and the lowest layer of the batches 28. An upper interleaved element can be provided between the top of the outer covering 14 and the highest layer of the batches 28. These interleaved elements are not considered to be packagings 22 in the sense of the invention.

Such interleaved elements can be rigid and they allow solidifying the package 10, which is particularly useful during its transport. Such interleaved elements can also be provided between the different layers of batches 28, allowing thus a better stabilization of the package 10, notably when spaces 32 are provided between the batches 28. These different interleaved elements can also be provided for the purpose of absorbing moisture or resisting the moisture. For example, the interleaved elements can be made of plastic; preferably, they have a low thermal insulation capacity in order not to compromise the cooling of the products.

The package 10 described above can be obtained by a method of packaging solid yeast products which may comprise the following steps:
  the provision of a support element 12;
  the packaging of solid yeast products in one or more packagings 22;
  the placing on the support element 12 of the solid yeast products contained in the packagings 22; and
  the placing of an outer covering 14 around the whole solid yeast products contained in the packagings 22.

The method can comprise further a step of grouping the solid yeast products into packs 26 in at least one packaging 22.

The method can further comprise a step of tying the packs 26 together in batches 28, preferably by means of one or more connecting bands 30, prior to placing on the support element 12 their wrapping the solid yeast products.

When placing on the support element 12 the solid yeast products, spaces 32 can be provided between the batches 28. This can be achieved by a particular arrangement of the batches 28 on the support element 12. Conversely, during placing on the support element 12 the solid yeast products, the batches 28 can be tightened to one another.

When placing on the support element 12 the solid yeast products, the batches 28 can be arranged on the support element 12 in a plurality of layers.

The different steps of the packaging can be carried out with the aid of palletizing tools known in the prior art. It should also be noted that at least one part of the steps of such a packaging method can be carried out in a cold chamber, that is to say with an external temperature less than or equal to 15° C., preferably less than or equal to 10° C., and notably less than or equal to 5° C. In particular, the final step of placing outer covering 14 can be carried out in a cold chamber or before entry into a cold chamber.

After the completion of such packaging method, the resulting packaging 10 can be stored until its use at a storage temperature which is less than or equal to 15° C., preferably less than or equal to 10° C., preferably less than or equal to 5° C.

The storage temperature is the external temperature to which the package is subjected (the temperature of the cold chamber) during at least 90% of the time, preferably during at least 95% or during at least 99% of the time. It is therefore not excluded that the package may be briefly subjected to a temperature above the aforementioned values, for example if it is moved from one cold chamber to another.

The step of storing the package can comprise the transport of the package (at the aforementioned storage temperature).

The storage time (until use) is preferably a period comprised between 1 day and 7 weeks, more particularly between 1 week and 7 weeks.

The invention allows advantageously storing each solid yeast product in the package at a temperature (local or real) less than or equal to 15° C., preferably less than or equal to 12° C., and more particularly preferably less than or equal to 10° C. throughout all the storage time.

The solid yeast products can be used for the production of bread-making products and notably for making bread, pastries, sweetened dough products and/or pizza dough.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

The following examples illustrate the invention without limiting it.

Example 1

Monitoring the Temperature on the Packages According to the Invention

1. Material

In this test, two packages according to the invention were used, and the variation of the local temperature inside the packages was measured by means of temperature probes while the packages were stored in a cold chamber.

The first package conforms to FIGS. 1 and 2, with a plastic support element. The package comprises five layers of ten batches, the batches which may comprise six packs each (in three rows of two packs). The packs of a batch are tied together by four crossed bands. Each pack comprised five solid yeast products, and had a weight of approximately 2.5 kg. Spaces were organized between the batches (cooling passages).

The second package was identical to the first, but had no cooling passages. In other words, the batches were tightened to one another.

The two packages were each provided with an outer covering composed of plastic film, covering the batches completely.

The outer covering was made of linear low-density polyethylene having the following characteristics: thickness of 23.3 μm, elastic modulus of 85.5 N/mm$^2$, tear resistance of 3000 mN.

The cellophane used has a paper density of 33.5 g/m$^2$ and a thickness of 23.3 μm (it would also be possible to replace it with a cellophane having a paper density of 43 g/m$^2$ and a thickness of 29.9 μm).

The two packages are respectively placed in a cold chamber and the temperature of the packages is monitored for eight days. In the following, the layers of the packages are numbered in ascending order from the bottom upwards (the first layer being in contact with the support element).

2. Results

Figure 3:
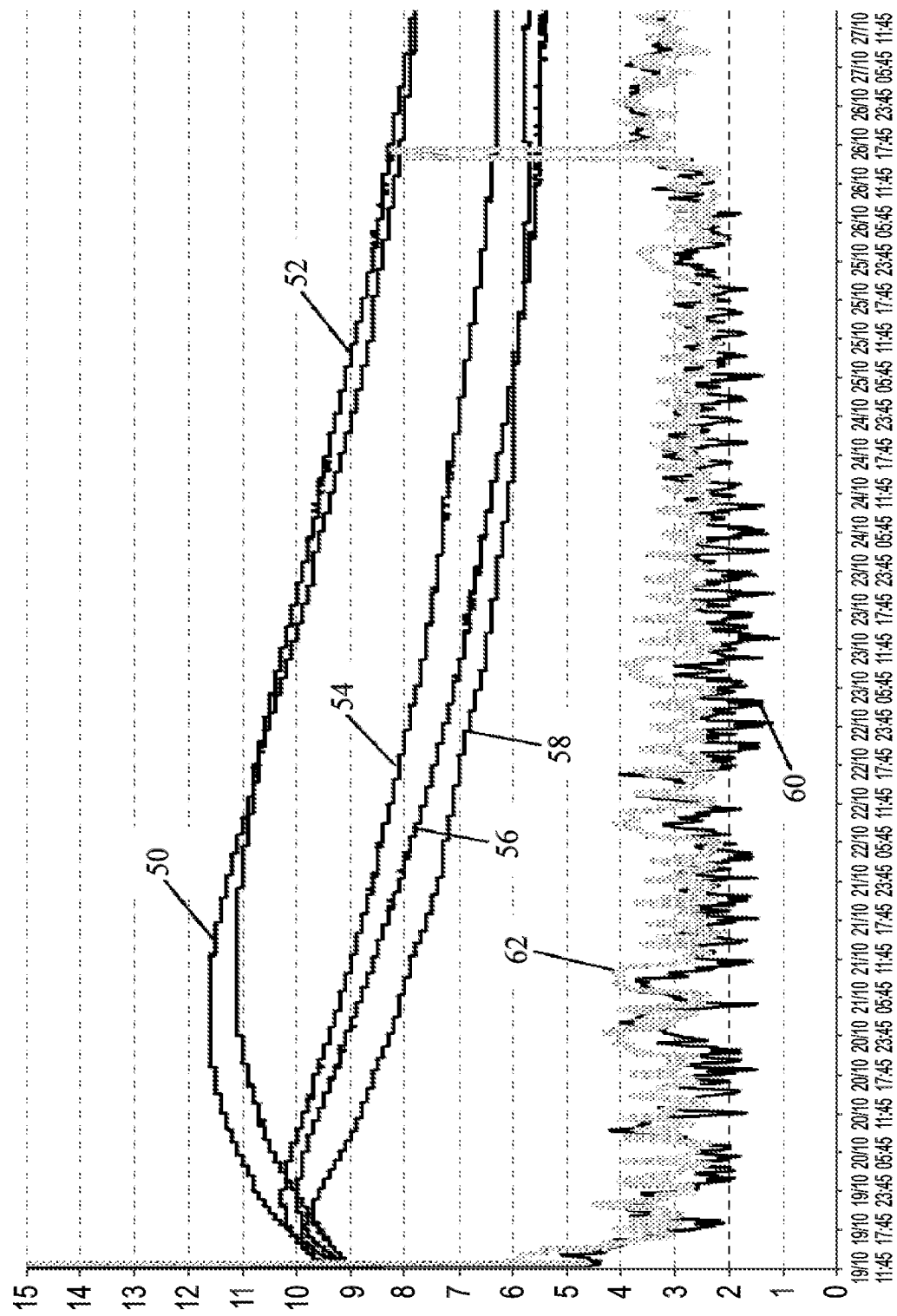
FIGS. 3-5 show the results of temperature tests conducted on different packages during their storage. The dates and times of the measurements are shown on the horizontal axis, and the results of the temperature measurements, in degrees Celsius, are shown on the vertical axis.

The curves of temperature evolution as a function of time are shown in FIG. 3. The table below provides a summary of the locations where the temperature was measured:

| References in the FIG. | Nature of the curve |
| --- | --- |
| 50 | Temperature at the center of the first package |
| 52 | Temperature at the center of the second package |
| 54 | Temperature in the fifth layer of the second package |
| 56 | Temperature in the first layer of the second package |
| 58 | Temperature in the first layer of the first package |
| 60 | Ambient temperature in the first room |
| 62 | Ambient temperature in the second room |

It can be observed that the local temperature in the package (and therefore the temperature of the solid yeast products) was satisfactorily maintained at a level of less than 12° C. (and mainly less than 10° C.) throughout the storage period at each position in the package.

Furthermore, the obtained cooling essentially does not depend on the presence or absence of the cooling passages.

Example 2 (Comparative)

Monitoring the Temperature on the Packages According to the Prior Art Packages 1. Material Tests were conducted to monitor the variation of the local temperature within packages using cardboard packagings which were stored in a cold chamber for eight days.

These packages were arranged in a similar way to the packages of Example 1, except that they have ten layers of cardboard boxes, each containing four packs.

The cardboard boxes used were Kaysersberg cardboard boxes with a 140×B140×180format, a paper density of 501.8 g/m$^2$, a bursting strength of 730 kPa, a stacking strength of 5.4 kN/m, and a thickness of 2.8 mm, and Smurfit cardboard boxes with a 200×140×140 format, a paper density of 522 g/m$^2$, a bursting strength of 1515 kPa, a ETC of 4.8 kN/m, and a thickness of 2.9 mm.

Each of the packages, shown as A to D below, also had distinctive properties which are summarized in the table below.

| Package | Special features |
|---|---|
| A | Presence of an outer covering (plastic film) covering all the cardboard boxes<br>No cooling passages |
| B | No outer covering<br>No cooling passages |
| C | Presence of an outer covering<br>Presence of cooling passages |
| D | No outer covering<br>Presence of cooling passages |

2. Results

Figure 4:
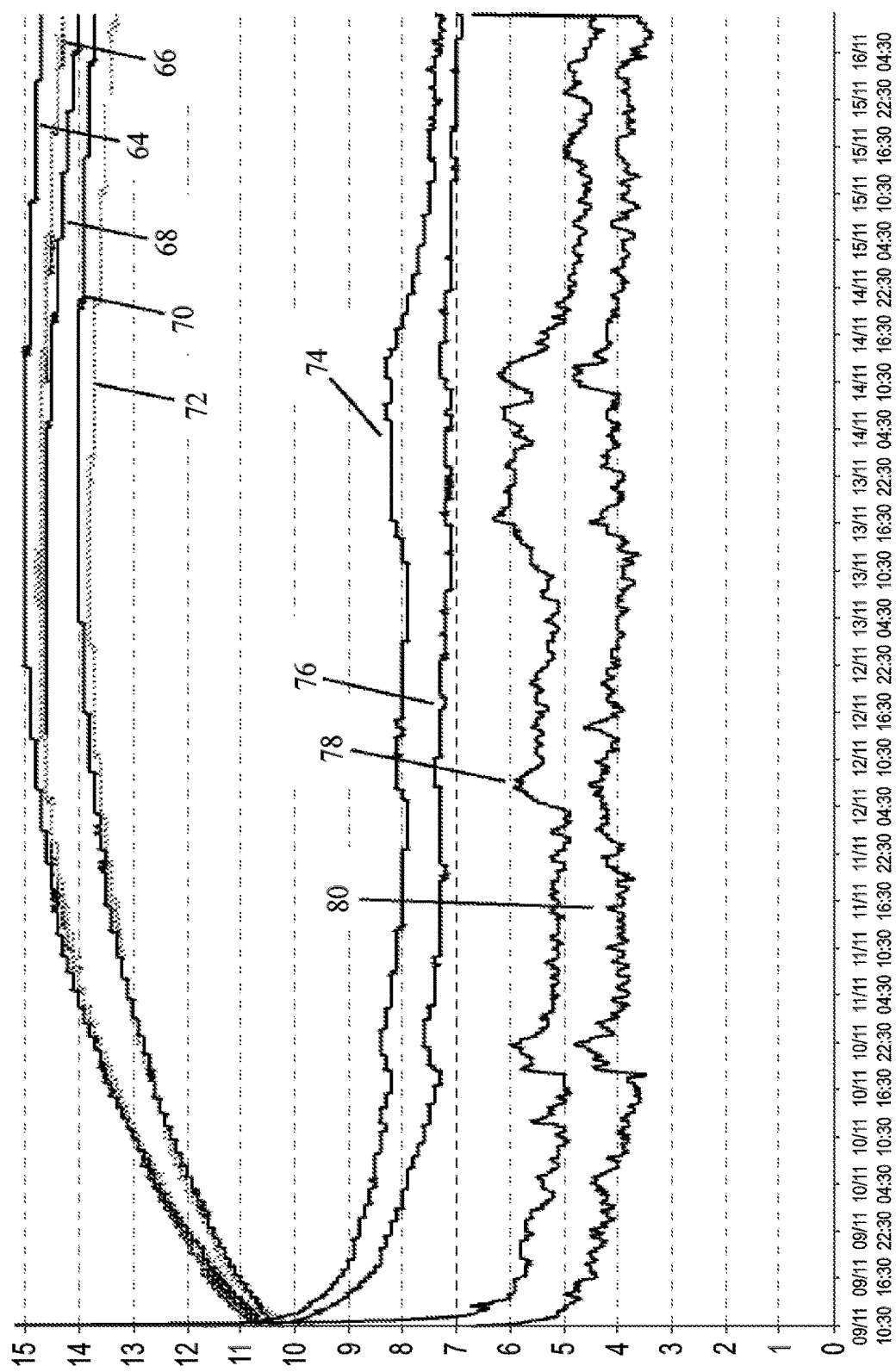
Figure 5:
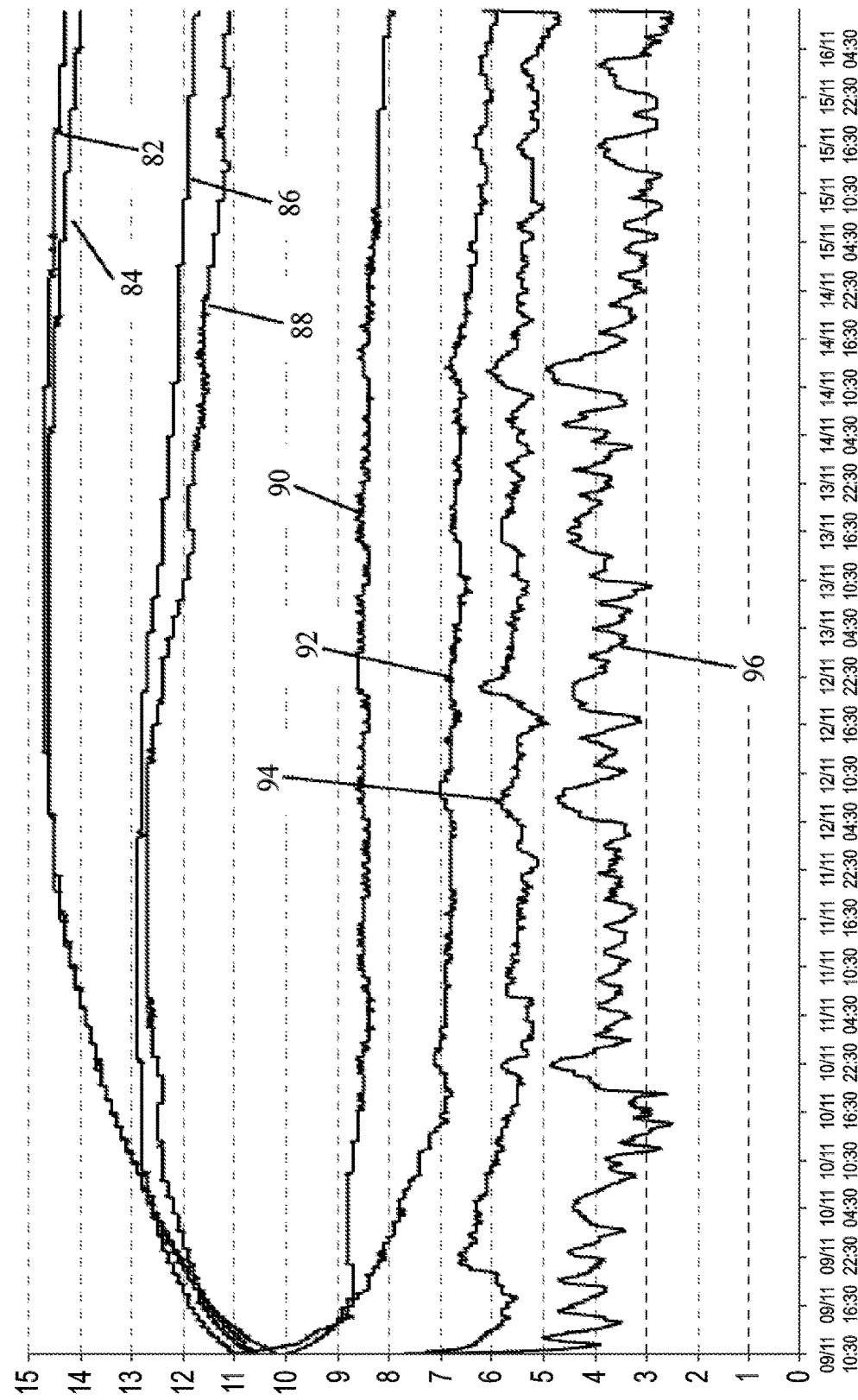

The curves of temperature variation as a function of time are shown in FIGS. 4 and 5. The table below shows a summary of the locations where the temperature was measured in order to provide the curves in FIGS. 4 and 5:

| References in the FIGS. | Nature of the curve |
|---|---|
| 64 | Temperature in the 6th layer of package B |
| 66 | Temperature in the 5th layer of package B |
| 70 | Temperature in the 6th layer of package A |
| 72 | Temperature in the 5th layer of package A |
| 74 | Temperature in the 10th layer of package A |
| 76 | Temperature in the 10th layer of package B |
| 78 | Ambient temperature in the cold chamber of package A |
| 80 | Ambient temperature in the cold chamber of package B |
| 82 | Temperature in the 6th layer of package C |
| 84 | Temperature in the 5th layer of package C |
| 86 | Temperature in the 6th layer of package D |
| 88 | Temperature in the 5th layer of package D |
| 90 | Temperature in the 10th layer of package C |
| 92 | Temperature in the 10th layer of package D |
| 94 | Ambient temperature in the cold chamber of package C |
| 96 | Ambient temperature in the cold chamber of package D |

The cooling less effective than with the packages of Example 1 is generally observed, at the position of the intermediate layers.

The presence of an outer covering on a package without cooling passage did not appear to cause any additional heating. However, alteration of the cardboard was found, due to excess moisture inside the covering.

For the packages with cooling passages, the plastic film prevents ventilation at the center of the package and cause unsatisfactory heating.

The invention is further described by the following numbered paragraphs:

1. A package (10) of solid yeast products comprising:
   a support element (12);
   solid yeast products contained in one or more packagings (22), supported by the support element (12);
   an outer covering (14) maintaining the whole solid yeast products contained in the packagings (22) on the support element (12);
   wherein the totality of the packagings (22) present between the solid yeast products and the outer covering (14) has a mass per unit surface area less than or equal to 200 g/m2.
2. The package (10) according to paragraph 1, wherein the totality of the packagings (22) present between the solid yeast products and the outer covering (14) has:
   a mass per unit surface area less than or equal to 150 g/m2, preferably less than or equal to 100 g/m2, and more particularly preferably less than or equal to 80 g/m2; and/or
   a thickness less than or equal to 150 μm, preferably less than or equal to 120 μm, more particularly preferably less than or equal to 90 μm.
3. The package (10) according to paragraph 1 or 2, wherein the packagings (22) are made of materials chosen from cellophane, paper, food-grade plastic film, and textile, and preferably chosen from cellophane and paper.
4. The package (10) according to any one of paragraphs 1 to 3, wherein the outer covering (14) is made of a stretchable plastic material, preferably single-stretched or double-stretched polyethylene.
5. The package (10) according to any one of paragraphs 1 to 4, wherein the solid yeast products are grouped in packs (26), each pack (26) being contained in at least one packaging (22), and the packs (26) are preferably grouped into batches (28), the packs (26) of each batch (28) being preferably tied between them, preferably by means of one or more connecting bands (30).
6. The package (10) according to paragraph 5, wherein:
   spaces (32) are provided between at least some of the batches (28); or
   the whole batches (28) are arranged without spaces between them.
7. The package (10) according to paragraph 5 or 6, wherein the batches (28) are arranged on the support element (12) in a plurality of superimposed layers.
8. The package (10) according to paragraph 7, comprising five layers, wherein:
   each layer comprises ten batches (28);
   each batch (28) comprises six packs (26), preferably distributed in three rows of two packs (26), the packs (26) of each batch (28) being preferably tied by two connecting bands (30) essentially parallel and two other connecting bands (30) essentially parallel which cross the preceding ones; and
   each pack (26) comprises five solid yeast products.
9. The package (10) according to any one of paragraphs 1 to 8, wherein the solid yeast products are compressed yeast, preferably comprising 27% to 34% of dry matter.
10. A method of packaging solid yeast products, comprising the following steps:
    the provision of a support element (12);
    the packaging of solid yeast products in one or more packagings (22);
    the placing on the support element (12) of the solid yeast products contained in the packagings (22);
    the placing of an outer covering (14) around the whole solid yeast products contained in the packagings (22);
    wherein the totality of the packaging (22) present between the solid yeast products and the outer covering (14) has a mass per unit surface area less than or equal to 200 g/m2.
11. The method according to paragraph 10, wherein the totality of the packagings (22) present between the solid yeast products and the outer covering (14) has:
    a mass per unit surface area less than or equal to 150 g/m2, preferably less than or equal to 100 g/m2, and more particularly preferably less than or equal to 80 g/m2; and/or
    a thickness less than or equal to 150 μm, preferably less than or equal to 120 μm, and more particularly preferably less than or equal to 90 μm.

12. The method according to paragraph 10 or 11, wherein:
    the packagings (22) are made of materials chosen from cellophane, paper, food-grade plastic film, and textile, and preferably chosen from cellophane and paper; and/or
    the outer covering (14) is made of a stretchable plastic material, preferably single-stretched or double-stretched polyethylene.
13. The method according to any one of paragraphs 10 to 12, comprising, before the step of placing on the support element (12) the solid yeast products contained in the packagings (22):
    a step of grouping the solid yeast products into packs (26), each pack being contained in at least one packaging (22); and
    a step of grouping the packs (26) into batches (28), the packs (26) of each batch (28) being preferably tied between them, preferably by means of one or more connecting bands (30);
    and wherein, preferably, the step of placing on the support element (12) the solid yeast products contained in the packagings (22) comprises the placing of the batches (28) on the support element (12) in superimposed layers.
14. The method according to paragraph 13, wherein, when placing on the support element (12) the solid yeast products contained in the packagings (22),
    spaces (32) are provided between the batches (28); or
    the whole batches (28) are arranged without spaces between them.
15. The packaging method according to any one of paragraphs 10 to 14, wherein the solid yeast products are compressed yeast, preferably comprising 27% to 34% of dry matter.
16. A method of storing and using solid yeast products, comprising the following steps:
    packaging solid yeast products in a package (10) according to any one of paragraphs 1 to 9, preferably by a packaging method according to any one of paragraphs 11 to 15;
    storing said package (10) of solid yeast products, until their use, at an external temperature less than or equal to 15° C., preferably less than or equal to 10° C., and more particularly preferably less than or equal to 5° C.;
    using at least one of the solid yeast products.
17. The method according to paragraph 16, wherein the solid yeast products are transported during the storage step, and wherein the storage step has preferably a duration comprised between 1 day and 7 weeks, preferably between 1 week and 7 weeks.
18. The method according to paragraph 16 or 17, wherein the temperature of each solid yeast product remains less than or equal to 15° C., preferably less than or equal to 12° C., and more particularly preferably less than or equal to 10° C. during the storage step.
19. The method according to any one of paragraphs 16 to 18, wherein at least one solid yeast product is used for the production of a bread-making product.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of packaging compressed yeast products, comprising the following steps:
    the provision of a support element (12);
    the packaging of compressed yeast products in one or more packagings (22);
    the placing on the support element (12) of the compressed yeast products contained in the packagings (22);
    the placing of an outer covering (14) around the whole solid yeast products contained in the packagings (22);
    wherein the totality of the packaging (22) present between the compressed yeast products and the outer covering (14) has a mass per unit surface area less than or equal to 200 g/m² and is partially gas permeable and liquid permeable.
2. The method according to claim 1, wherein the totality of the packagings (22) present between the compressed yeast products and the outer covering (14) has:
    a mass per unit surface area less than or equal to 150 g/m², preferably less than or equal to 100 g/m²; and/or
    a thickness less than or equal to 150 μmm.
3. The method according to claim 1 wherein:
    the packagings (22) are made of materials chosen from cellophane, paper, food-grade plastic film, and textile; and/or
    the outer covering (14) is made of a stretchable plastic material.
4. The method according to claim 1, comprising, before the step of placing on the support element (12) the compressed yeast products contained in the packagings (22):
    a step of grouping the compressed yeast products into packs (26), each pack being contained in at least one packaging (22); and
    a step of grouping the packs (26) into batches (28), the packs (26) of each batch (28) being preferably tied between them.
5. The method according to claim 4, wherein, when placing on the support element (12) the compressed yeast products contained in the packagings (22),
    spaces (32) are provided between the batches (28); or
    the whole batches (28) are arranged without spaces between them.
6. A method of storing compressed yeast products, comprising the following steps:
    packaging compressed yeast products according to claim 1,
    and storing at an external temperature less than or equal to 15° C. said package of solid yeast products, until their use.
7. The method according to claim 6, wherein the compressed yeast products are transported during the storage step, and wherein the storage step has a duration comprised between 1 day and 7 weeks.
8. The method according to claim 6, wherein the temperature of each compressed yeast product remains less than or equal to 15° C. during the storage step.
9. The method according to claim 6, wherein at least one compressed yeast product is used for the production of a bread-making product.
10. The method (10) according to claim 1, wherein the compressed yeast products are compressed yeast and comprise 27% to 34% of dry matter.
11. The method according to claim 1, comprising, before the step of placing on the support element (12) the compressed yeast products contained in the packagings (22):
    a step of grouping the compressed yeast products into packs (26), each pack being contained in at least one packaging (22); and
    a step of grouping the packs (26) into batches (28), the packs (26) of each batch (28) being tied between them;

and wherein the step of placing on the support element (12) the compressed yeast products contained in the packagings (22) comprises the placing of the batches (28) on the support element (12) in superimposed layers.

12. The method according to claim 11, wherein the packs (26) of each batch (28) being tied between them by means of one or more connecting bands (30).

13. A method of storing compressed yeast products comprising performing the packaging method of claim 2 to obtain packaged compressed yeast products and storing at an external temperature less than or equal to 15° C. said packaged compressed yeast products until use.

* * * * *